United States Patent
Kim et al.

(10) Patent No.: US 10,980,842 B2
(45) Date of Patent: Apr. 20, 2021

(54) COMPOSITION FOR PROMOTNG BONE FORMATION WITH FERMENTED OYSTERS AND SEAWEED

(71) Applicant: Jeju National University Industry-Academic Cooperation Foundation, Jeju-si (KR)

(72) Inventors: Gi-Young Kim, Jeju-si (KR); Yung Hyun Choi, Busan (KR); Eui Kyun Park, Daegu (KR); Bae Jin Lee, Busan (KR); You-Jin Jeon, Jeju-si (KR)

(73) Assignee: JEJU NATIONAL UNIVERSITY INDUSTRY-ACADEMIC COOPERATION FOUNDATION, Jeju-si (KR)

( * ) Notice: Subject to any disclaimer, the term of this patent is extended or adjusted under 35 U.S.C. 154(b) by 0 days.

(21) Appl. No.: 16/441,131

(22) Filed: Jun. 14, 2019

(65) Prior Publication Data

US 2019/0381108 A1    Dec. 19, 2019

(30) Foreign Application Priority Data

Jun. 15, 2018    (KR) ........................ 10-2018-0069132

(51) Int. Cl.
| | |
|---|---|
| *A61K 35/68* | (2006.01) |
| *A61K 35/618* | (2015.01) |
| *A23L 17/60* | (2016.01) |
| *A23L 17/40* | (2016.01) |
| *A61P 19/10* | (2006.01) |
| *A61K 31/145* | (2006.01) |
| *A61K 31/197* | (2006.01) |
| *A61K 31/729* | (2006.01) |
| *A61K 36/03* | (2006.01) |
| *A61K 36/04* | (2006.01) |
| *A61K 36/05* | (2006.01) |

(52) U.S. Cl.
CPC ............ *A61K 35/618* (2013.01); *A23L 17/40* (2016.08); *A23L 17/60* (2016.08); *A61K 31/145* (2013.01); *A61K 31/197* (2013.01); *A61K 31/729* (2013.01); *A61K 36/03* (2013.01); *A61K 36/04* (2013.01); *A61K 36/05* (2013.01); *A61P 19/10* (2018.01); *A23V 2002/00* (2013.01); *A23V 2200/306* (2013.01); *A23V 2250/202* (2013.01); *A23V 2250/2042* (2013.01)

(58) Field of Classification Search
None
See application file for complete search history.

(56) References Cited

FOREIGN PATENT DOCUMENTS

| KR | 10-2011-0077807 | * | 7/2011 |
| KR | 10-2012-0095150 | * | 9/2012 |
| KR | 2015 062749 A | * | 6/2015 |
| KR | 1020170116402 A | | 10/2017 |
| WO | WO 2010 027117 | * | 3/2010 |

* cited by examiner

*Primary Examiner* — Ralph J Gitomer
(74) *Attorney, Agent, or Firm* — STIP Law Group, LLC

(57) ABSTRACT

The present invention relates to a composition for improving bone health, and the composition includes a fermented extract extracted from a fermented material of oysters, which is obtained by fermenting oysters, and the fermented extract may promote bone formation by suppressing the activity of osteoclasts and promoting the activity of osteoblasts.

The composition contains large amounts of taurine and vitamins, and natural gamma-aminobutyric acid.

5 Claims, 13 Drawing Sheets

FIG. 3A
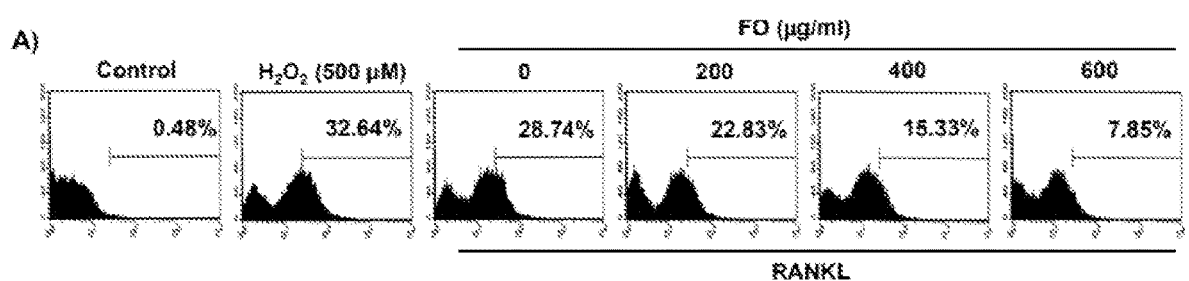
FIG. 3B
FIG. 3C
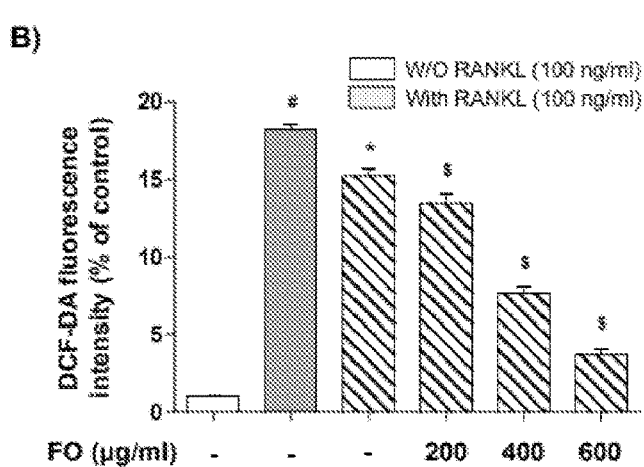
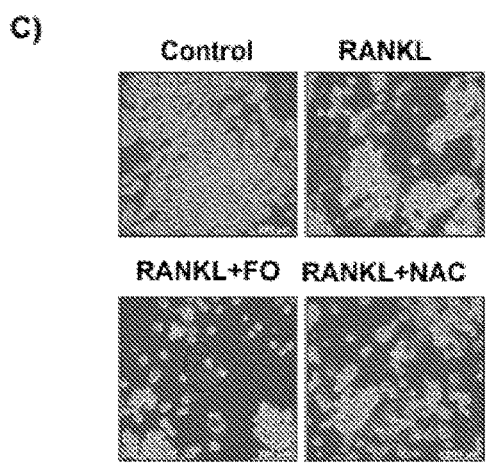

COMPOSITION FOR PROMOTNG BONE FORMATION WITH FERMENTED OYSTERS AND SEAWEED

CROSS-REFERENCE TO RELATED APPLICATIONS

This application claims priority to and the benefit of Korean Patent Application No. 10-2018-0069132 filed in the Korean Intellectual Property Office on Jun. 15, 2018, the entire contents of which are incorporated herein by reference.

TECHNICAL FIELD

The present invention relates to a composition for improving bone health, including a functional fermented material using oysters. More specifically, the present invention relates to a composition for improving bone heath, which prepares a functional fermented material using oysters and includes a functional fermented material using oysters that are excellent in effects of promoting bone formation and preventing and treating osteoporosis with the functional fermented material.

BACKGROUND ART

Bone tissue is a dynamic tissue in which resorption and formation continue in order to maintain bone mass and skeletal homeostasis. Two types of cells having special functions are involved in bone remodeling.

Osteoclasts resorb bone, whereas osteoblasts serve to synthesize and fill bone matrix. Accordingly, bone mass depends on the reciprocal function of these cells. A typical adult always maintains a balance between the amount of bone resorption and the amount of bone formation.

Bone remodeling occurs through a constant cycle, and occurs in locally narrow sites to maintain the structure of the skeletal system, and the structure and function of the skeletal system are regulated by complex interactions between systemic hormones and local factors (Canalis, E., McCarthy, T. and Centrella, M.: Growth Factors and The regulation of bone remodeling. J. Clin. Invest. 81:277-281 (1988), Raisz, L. G.: Hormonal regulation of bone growth and remodeling, in Cell and Molecular Biology of Vertebrate Hard Tissue CIBA Foundation Symposium 136, pp 226-238, Wiley, NY (1988)).

An imbalance between the activity of osteoblasts and the activity of osteoclasts appears as skeletal abnormalities due to a decrease (osteoporosis) or an increase (osteosclerosis) of the entire bone. Various theories and claims have been raised as to whether such a bone metabolism imbalance is primarily due to a reduction in function of osteoblasts or an increase in bone resorption, that is, an enhancement of activity of osteoclasts, and examples of factors of osteoporosis include the increase in age, nutritional deficiency, lack of exercise, lack of calcium intake, genetic factors, drug use, hormone effects, and the like (Ryan P J, Evans P, Gibson T, Fogelman I. Osteoporosis and chronic back pain: A study with single-photon emission computed tomography bone scintigraphy. J Bone Miner Res. 7: 1455-1460 (1992)).

Among bone metabolic diseases, osteoporosis, which appears as a major issue in the aging society, is a disease in which the bone mass in a unit volume decreases without any significant change in chemical composition of bone, and as a result, even a slight impact may easily cause bone fracture. In the case of elderly people, particularly, postmenopausal women, the occurrence frequency thereof is known to be highest due to the lack of secretion of estrogen (Jilka R L. Cytokines, bone remodeling and estrogen deficiency. Bone 23: 75-81 (1998)). However, even men tend to reduce bone mass as men age (Stein G S, Lian J B, van Wijnen A J, Montechino M. Transcriptional control of osteoblast growth and differentiation. Physiol Rew. 76: 593-629 (1996)).

Recently, the fracture rate of elementary and junior high school students has more than doubled in the last 20 years. It is very important to increase bone mass from a young age in terms of prevention or treatment of bone diseases caused by bone metabolism imbalance, and it is an important issue regardless of gender or age to maintain the health of bones as described above.

Since most of the drugs currently used for prevention and treatment of osteoporosis act to suppress bone resorption, already advanced bone loss cannot be completely restored, and accordingly, the complete prevention of the occurrence of osteoporosis, which is an ultimate goal, cannot be achieved. Thus, studies on the increase in bone formation has recently been drawing attention for prevention and treatment of osteoporosis, and there is a need for a scientific approach for effects on the ability to regenerate bone tissues (Cho S H, Kim K G, Kim S R, Lee J A, Moon H, Hwang Y Y. The effects of 17-estradiol, medroxyprogesterone acetate and parathyroid hormone on the differentiation of osteoblast cell. Korean J Obstet Gynecol. 39: 1497-1506 (1996), Boonen A, Broos P, Deqeker J. The prevention of treatment of age-related osteoporosis in the elderly by systemic recombinant growth factor therapy (rhIGF-I or rhRGF-): a perspective. J Internal Medicine. 242: 285-290 (1997)).

Therefore, there is a need for developing a composition for improving bone health, which is excellent in effects of promoting bone formation by suppressing the activity of bone-destructing cells and activating bone-forming cells, and thus may prevent and suppress the occurrence of osteoporosis.

PRIOR ART DOCUMENT

Patent Document (Patent Document 1) (Patent Document 1) KR 10-2017-0116402 A1

SUMMARY OF THE INVENTION

An object of the present invention is to provide a composition for improving bone health, including a functional fermented material using oysters.

Another object of the present invention is to provide a composition for improving bone health, including a functional fermented material containing large amounts of taurine and vitamins and containing natural gamma-aminobutyric acid (GABA) and seaweed oligosaccharides from seaweed using oysters.

Still another object of the present invention is to provide a composition for improving bone health, including a functional fermented material using oysters, which may exhibit a bone formation effect by suppressing the activity of osteoclasts and promoting the activity of osteoblast.

Yet another object of the present invention is to provide a composition for improving bone health, including a functional fermented material using oysters that are excellent in effects of preventing and suppressing the occurrence of osteoporosis. In order to achieve the objects, the composition for improving bone health, including a functional fermented material using oysters according to an exemplary embodiment of the present invention includes a fermented extract extracted from a fermented material of oysters and seaweed, which is obtained by fermenting oysters and seaweed, and the fermented extract may promote bone formation by suppressing the activity of osteoclasts and promoting the activity of osteoblasts.

The fermented extract includes taurine and gamma-aminobutyric acid (GABA).

The oysters may be selected from the group consisting of raw oysters, a hydrolysate of oysters, an extracted concentrate of oysters, and a mixture thereof.

The seaweed may be selected from the group consisting of sea tangle, algue brune, brown seaweed, brown seaweed stem, agar, green laver, glue plant, gracilaria, *Capsosiphon fulvescens*, and a mixture thereof.

The fermented material of oysters and seaweeds may be fermented using a fermentation microbe, and the fermentation microbe may be selected from the group consisting of *lactobacillus*, yeast, and a mixture thereof.

A pharmaceutical composition including the functional fermented material using oysters according to another exemplary embodiment of the present invention may include the composition for improving bone health.

A food composition including the functional fermented material using oysters according to still another exemplary embodiment of the present invention may include the composition for improving bone health.

Hereinafter, the present invention will be described in more detail.

The composition for improving bone health, including a functional fermented material using oysters according to an exemplary embodiment of the present invention includes a fermented extract extracted from a fermented material of oysters and seaweed, which is obtained by fermenting oysters and seaweed, and the fermented extract may promote bone formation by suppressing the activity of osteoclasts and promoting the activity of osteoblasts.

A fermented extract is prepared using a fermented material obtained by fermenting the oysters and seaweed, and may be used as a use for improving bone health.

More specifically, the present invention relates to a composition for improving bone health, including taurine, seaweed oligosaccharide, and natural GABA as main components by extracting taurine from oysters and extracting seaweed oligosaccharides and natural GABA from seaweeds.

The composition for improving bone health of the present invention may be subjected to a fermentation process to remove seaweed odor and fish-like odor, thereby providing a composition which is excellent in taste and flavor when used for food.

The oyster contains various nutrients such as glycogen, vitamins, and proteins, is recognized as a perfect food which is rich in not only 18 or more amino acids such as tyrosine and glutamic acid and a functional material such as taurine, but also an essential mineral such as iron and iodine, and has been widely used as one of the 10 global marine products. The oysters mass-cultured on the Korean south coast including Tongyeong was a main contributor to export earnings for Korea in the early period of economic development in the 1960s and 1970s, but recently, Chinese oysters have rapidly made inroads into the world market, and have been distributed in the form of a frozen or simple processed product.

The demand for seaweeds has been growing along with the functionality thereof, and in particular, the potential possibility thereof has been highlighted along with reports that seaweed are effective for antibacterial, antioxidant, antiviral, and anticancer activities and for the prevention of lifestyle diseases such as arteriosclerosis, myocardial infarction, hypertension, angina pectoris, and stroke due to abundant minerals and functional polysaccharides, and among seaweed, sea tangle is a natural raw material containing a large amount of glutamic acid which is a precursor of GABA along with oysters, and sea tangle-derived natural GABA may be produced at a high concentration by a fermentation process without an artificial addition of MSG (chemical synthetic product), which is a production method in the related art for the production of natural GABA at a high concentration.

Simultaneously, a fermentation process by microbes contains both a monosaccharide such as brown algae—derived fucose and a functional low-molecular oligosaccharide through low-molecularization of polymer functional seaweed polysaccharides such as fucoidan.

Seaweeds contain large amounts of amino acids (such as glutamic acid and aspartic acid), have been recognized as an ideal natural food because seaweeds are also rich in seaweed oligosaccharides (such as fucoidan) which have been in the limelight as a highly functional natural material, and contain abundant amounts of various minerals, vitamins, and the like, and Korean and foreign experts have recently performed active studies on the physiological effectiveness of seaweed, and as a result, it has been revealed that seaweeds are deeply involved in diet action, treatment of constipation by intestinal regulation, release of heavy metals and radioactive materials from the body, and the like. Furthermore, it has been reported that sulfur-containing polysaccharides collectively referred to as fucoidan are effective for antibacterial, antioxidant, antiviral, and anticancer activities and for the prevention of adult diseases such as arteriosclerosis, myocardial infarction, hypertension, angina pectoris, and stroke.

However, the use of marine resources such as seaweeds and oysters is mostly limited to primary processed products such as simply dried products or feed. When seaweeds are used only as primary processed products such as simply dried products or feed as described above, there occurs a problem in that various physiologically active materials present in marine resources such as seaweeds and oysters may not be maximally utilized, and there is a problem in that natural components such as abundant vitamins or minerals may not be maintained as they are.

Thus, in the present invention, as a fermented extract extracted from a fermented material of oysters and seaweeds fermented using seaweeds and oysters is used, various physiologically active materials present in seaweeds and oysters may be maximally utilized, and natural components such as abundant vitamins or minerals may be maintained as they are.

Gamma-aminobutyric acid (GABA) is a type of non-proteinogenic amino acid which has a molecular weight of 103.2 daltons, is called piperic acid, is usually stable to heat due to a melting point of 202° C., has a molecular formula of $C_4H_9NO_2$, and has high solubility to water, and is an excitatory inhibitory neurotransmitter present in the brain or spinal cord of a mammal. GABA is known to be involved in the regulation of many physiological mechanisms of the human body to accelerate the metabolic function of brain cells by activating the blood flow of the brain and increasing the oxygen supply.

GABA is known to be also involved in the secretory regulation of growth hormones and involved in various physiological regulatory actions such as drop in blood pressure, pain alleviation, mental stabilization action, liver and kidney function improvement action, and colorectal cancer inhibitory action, and thus is a material which receives much pharmacological attention. However, in general, the amounts of taurine and GABA ingested through food and the like are not great, so that it is not easy to ingest an amount required for exhibiting pharmacological action from food.

Thus, the present invention intends to make polymer seaweed polysaccharides such as fucoidan, which are useful for the human body, low molecules by a fermentation process using a fermentation strain which does not affect a functional material such as taurine in addition to glutamic acid while converting glutamic acid present in oysters and seaweeds into GABA in a large amount, such that taurine and GABA limited in amount by natural ingestion may be ingested up to an amount expected to be physiologically active, and to prepare a functional fermented material containing large amounts of taurine and natural GABA and seaweed minerals including low-molecular seaweed oligosaccharides while maintaining the preference as a functional food material in the related art by removing off-taste and off-flavor such as seaweed odor and fish-like odor inevitably occurring during the extraction and processing of oysters and seaweed, thereby providing the functional fermented material as a composition for improving bone health.

The oysters and seaweeds used in the present invention have the same pre-treatment process of washing, desalting, and grinding, and as oysters, it is possible to use raw oysters, a hydrolysate of oysters, or an extracted concentrate of oysters. When the content of oysters, seaweed, or a mixture thereof is more than 30% (v/v), the taste of a final composition is affected from the salts of oysters and seaweeds, so that the content of oysters, seaweed, or a mixture thereof is suitably 10 to 30% (v/v).

Specifically, it is preferred that when oysters, a hydrolysate of oysters, an extracted concentrate of oysters, and seaweeds are used alone as a fermentation source, the content thereof is 10 to 30% (v/v) of the total weight, and when a mixture thereof is fermented as a fermentation source, for the ratio of oysters, hydrolysate of oysters, or extracted concentrate of oysters and seaweeds selectively mixed and added in an amount of 10 to 30% (v/v), the oysters, the hydrolysate of oysters, or the extracted concentrate of oysters and the seaweeds are selectively used in a range of 1:2 to 2:1.

The oysters may be selected from the group consisting of raw oysters, a hydrolysate of oysters, an extracted concentrate of oysters, and a mixture thereof.

The hydrolysate of oysters may be prepared by a preparation method including: hydrolyzing pre-treated oysters by mixing water with the pre-treated oysters, and then adding alcalase thereto while stirring the mixture at a temperature of 50 to 70° C.; removing a residue of the hydrolyzed oysters by a vibration sieve of 40 to 200 mesh and collecting a hydrolysate of oysters; and finely filtering only water-soluble materials from the collected hydrolysate of oysters using an external circulation type vacuum separation membrane having a module with a pore size of 0.05 to 0.1 μm.

The preparation method may further include packing the finely filtered hydrolysate so as to be easily added after the finely filtering of the water-soluble materials.

The extracted concentrate of oysters may be prepared by a preparation method including: pre-treating oysters by a method of washing, desalting, and grinding; extracting the pre-treated oysters by mixing water with the pre-treated oysters under stirring at 70 to 90° C. for 20 to 60 minutes; removing a residue of the extracted oysters by a vibration sieve of 40 to 200 mesh and collecting an extract of oysters; finely filtering only water-soluble materials from the extract of oysters completely extracted using an external circulation type vacuum separation membrane having a module with a pore size of 0.05 to 0.1 μm; and concentrating the finely filtered extract of oysters so as to have a brix of 20 to 40% by reducing pressure at a temperature of 30 to 50° C.

After the concentrating of the finely filtered extract, the preparation method may further include packing the concentrated concentrate so as to be easily added.

The hydrolysate and extracted concentrate of oysters is subjected to a fine filtration process using an "external circulation type vacuum separation membrane device" which is a fine filtration device, so that only water-soluble materials of 0.05 to 0.1 um are filtered and used in a fermentation process, and the filtration system may be prevented from being exposed to the outside during the filtration process, thereby minimizing the loss of flavor generated during filtration.

Since the "external circulation type vacuum separation membrane system" is operated under a mild condition between 70 and 400 mmHg as a pressure reduction type by attaching a self-priming pump to a part from which a filtrate is discharged unlike an existing pressurization process as a membrane separation process which is separated from the outside environment to minimize the burden on the membrane according to the pressure and suction and filter the filtrate from a filtrate discharging part to the self-priming pump, the pump and the concentrate are not directly brought into contact with each other, the separation membrane system is always operated under low pressure and does not need a separate concentration tank, and costs of the plumbing, the valves, and the system are minimized, so that the separation membrane system is very economically feasible.

As the system is designed such that contaminants which may be adsorbed onto the external surface of the membrane may be continuously dropped by continuously discharging the air from the bottom of each membrane (module), the system has an advantage in that the system continuously has stable permeability without accelerating the contamination of the membrane as the filtration process is performed, and the system may also be manufactured by separating the filtrate into a fractional part.

The composition for improving bone health, including a functional fermented material using oysters according to the present invention may be prepared in the order of the steps of (1) preparing a medium by mixing water with oysters, a hydrolysate of oysters, or an extracted concentrate of oysters and pre-treated seaweeds such that the content thereof is 10 to 30% (v/v) based on the total weight, sterilizing the mixture, and cooling the mixture to 30 to 37° C.; (2) inoculating *lactobacillus*, yeast, and a mixture thereof as a fermentation microbe into the medium, and then fermenting the inoculated medium; (3) killing the logarithmically proliferated fermentation microbe during the fermentation period by sterilizing a fermentation solution completely fermented at high temperature under pressure; and (4) finely filtering only clear and clean water-soluble materials of 0.05 to 0.1 um from the sterilized fermentation solution.

The seaweeds may be selected from the group consisting of sea tangle, algue brune, brown seaweed, brown seaweed stem, agar, green laver, glue plant, gracilaria, *Capsosiphon fulvescens*, and a mixture thereof.

For the composition for improving bone health of the present invention, the aforementioned raw oysters or seaweeds may be added alone or in mixtures so as to have a content of 10 to 30% based on the total weight, pressurized and sterilized at high temperature at 115 to 125° C. for 15 to 20 minutes, and then cooled to 30 to 37° C. to mix *lactobacillus* and yeast as a fermentation microbe alone or in mixtures, inoculate the *lactobacillus*, the yeast, or a mixture thereof so as to have a content of 1 to 5% (v/v), and ferment the inoculated mixture for 2 to 7 days, thereby preparing a composition containing large amounts of taurine and natural GABA, minerals including seaweed oligosaccharides, and the like.

For the composition for improving bone health of the present invention, the aforementioned hydrolysate of oysters or seaweeds may be added alone or in mixtures so as to have a content of 10 to 30% based on the total weight, pressurized and sterilized at high temperature at 115 to 125° C. for 15 to 20 minutes, and then cooled to 30 to 37° C. to mix *lactobacillus* and yeast as a fermentation microbe alone or in mixtures, inoculate the *lactobacillus*, the yeast, or a mixture thereof so as to have a content of 1 to 5% (v/v), and ferment the inoculated mixture for 2 to 7 days, thereby preparing a composition containing large amounts of taurine and natural GABA, minerals including seaweed oligosaccharides, and the like.

For the composition for improving bone health of the present invention, the aforementioned extracted concentrate of oysters or seaweeds may be added alone or in mixtures so as to have a content of 10 to 30% based on the total weight, pressurized and sterilized at high temperature at 115 to 125° C. for 15 to 20 minutes, and then cooled to 30 to 37° C. to mix *lactobacillus* and yeast as a fermentation microbe alone or in mixtures, inoculate the *lactobacillus*, the yeast, or a mixture thereof so as to have a content of 1 to 5% (v/v), and ferment the inoculated mixture for 2 to 7 days, thereby preparing a composition containing large amounts of taurine and natural GABA, minerals including seaweed oligosaccharides, and the like.

The composition for improving bone health, including a functional fermented material using oysters according to the present invention may decrease the size of osteoclasts and may suppress the number of osteoclasts in a concentration-dependent manner. Since the actin of osteoclasts is organized as one big ring in order to divide a general extracellular space while osteoclasts perform bone formation during the bone resorption process and are attached to bones, the formation of the actin ring is an important mark for the ability of osteoclasts to resorb bones, and the composition of the present invention may suppress the formation of the actin ring of differentiated osteoclasts in a concentration-dependent manner.

It is possible to suppress the expression of proteins associated with the differentiation of osteoclasts.

According to the composition for improving bone health, including a functional fermented material using oysters according to the present invention, the expression of Alp, $RUNX_2$, Col1a1, OSX, Bglap, $BMP_2$, and BMP which are genes essential for the formation of osteoblasts is strongly increased. Further, the Alp activity, which is a core factor for bone formation, is increased.

The composition for improving bone health, including a functional fermented material using oysters according to the present invention is excellent in effects of suppressing a reduction in bone density and may prevent the destruction of bones. Furthermore, numerical values of the bone mineral density (BMD), the bone volume/trabecular volume (BV/TV), fibrous tissues in bones (the trabecular thickness) (Tb, Th (mm)), the trabecular number (Tb, N(1/mm)), and the trabecular spacing (Tb, Sp (mm)) are improved.

As an example of the *lactobacillus* and yeast used in the formation step, *Lactobacillus brevis* BJ20 (Accession No.: KCTC 11377BP) and *Saccharomyces cerevisiae* MBP-27 may be used.

It can be confirmed that the strain exhibits an excellent effect for removing off-taste and off-flavor such as seaweed odor, and the strain may exhibit an excellent effect for removing a functional fermented material which is excellent in antioxidant and antihypertensive effects.

However, when a fermented material was prepared using the *lactobacillus* and yeast, it was confirmed that the fermented material has an effect which is excellent in antioxidation and antihypertension, but it was confirmed through experiments that the fermented material does not exhibit a significant effect for the promotion of bone formation by suppressing the activity of osteoclasts, which affects bone health and promoting the activity of osteoblasts.

Thus, in the present invention, as the *lactobacillus* and yeast, it is possible to use *Lactobacillus fermentum* JS (strain accession No. KCCM10499) and *Aspergillus* Usamii.

It can be confirmed that the strain can exhibit an effect which is excellent in removing off-taste and off-flavor such as a seaweed odor, and it was confirmed that the strain exhibited a significant effect for promotion of bone formation by suppressing the activity of osteoclasts, which affects bone health and promoting the activity of osteoblasts.

A pharmaceutical composition according to another exemplary embodiment of the present invention may include a composition for improving bone health, including the functional fermented material using oysters.

The pharmaceutical composition of the present invention may include a pharmaceutically acceptable carrier. A composition including a pharmaceutically acceptable carrier may be various oral or parenteral dosage forms selected from the group consisting of a tablet, a pill, a powder, a granule, a capsule, a suspension, a liquid for internal use, an emulsion, a syrup, a sterilized aqueous solution, a non-aqueous solvent, a suspension, an emulsion, a freeze-dried preparation, and a suppository.

When the composition is prepared, the composition is prepared by using a diluent or excipient, such as a filler, an extender, a binder, a wetting agent, a disintegrant, and a surfactant, commonly used. A solid formulation for oral administration includes a tablet, a pill, a powder, a granule, a capsule, and the like, and the solid formulation is prepared by mixing at least one excipient, for example, starch, calcium carbonate, sucrose or lactose, gelatin, and the like with one or more compounds.

In addition to a simple excipient, lubricants such as magnesium stearate and talc may also be used. A liquid formulation for oral administration corresponds to a suspension, a liquid for internal use, an emulsion, a syrup, and the like, and the liquid formulation may include, in addition to water and liquid paraffin which are simple commonly used diluents, various excipients, for example, a wetting agent, a sweetener, an aromatic, a preservative, and the like.

Examples of a formulation for parenteral administration include an aqueous sterile solution, a non-aqueous solvent, a suspension, an emulsion, a freeze-dried preparation, and a suppository. As the non-aqueous solvent and the suspension solvent, it is possible to use propylene glycol, polyethylene glycol, a vegetable oil such as olive oil, an injectable ester such as ethyl oleate, and the like. As a base of the suppository, it is possible to use witepsol, Macrogol, Tween 61, cacao butter, laurin fat, glycerogelatin, and the like.

A food composition according to another exemplary embodiment of the present invention may include a composition for improving bone health, including the functional fermented material using oysters.

Since the composition for improving bone health according to the present invention is not toxic to the human body at all, the composition can be taken for a long period of time so that the composition may also be used as a health functional food. When the composition is prepared as a health functional food, the composition can be in the form included in a beverage, a snack and confectionary, gruel, and a soup, but the form is not limited thereto.

That is, when the composition for improving bone health according to the present invention is prepared as an aqueous solution, an aqueous suspension or a dosage form in the form of a typical internal use by dissolving the composition together with a typical sweetener, vitamins, amino acids, minerals, organic acids, an aromatic, a preservative, or the like, the composition may become an excellent health food capable of supplementing insufficient nutrients together with brain cell metabolism promotion and blood flow promotion.

Accordingly, it is possible to provide a new food obtained by containing the seaweed extract fermented liquid or seaweed fermented powder of the present invention as a main ingredient, adding one or more auxiliary ingredients selected from a herbal medicine extract, vitamins, amino acids, a sweetener, minerals, organic acids, an aromatic, a fruit juice, a preservative, or the like, if necessary, adding a suitable amount of water thereto and sterilizing the resulting mixture or preparing the resulting mixture as a dosage form in the form of a typical internal use.

The auxiliary ingredient which may be used in the present invention means an ingredient which may be typically used by the person skilled in the art, and is not limited thereto.

Preferably, the food composition of the present invention may further include an *Albizia julibrissin* extract and a licorice extract in order to increase the preference.

When the *Albizia julibrissin* extract and the licorice extract are further included, off-taste and off-flavor such as seaweed odor slightly remaining may be removed by the *Albizia julibrissin* extract and the licorice extract. Further, a food composition with high preference may be provided due to the sweet taste of licorice. However, when the licorice extract is used in mixture with the *Albizia julibrissin* extract, the inherent sweet taste of licorice may be enhanced as compared to the case where only licorice is used.

The *Albizia julibrissin* is a tree that symbolizes a couple's good chemistry, and is also referred to as silk tree, pink silk tree, night sleeper, and *mimosa* tree. For this reason, trees growing in the mountains and fields have been frequently planted as garden trees in the garden. Since the *Albizia julibrissin* was a tree used to make the handle of a wooden tool, the *Albizia julibrissin* is referred to as wooden tool tree, and there are places where the *Albizia julibrissin* is referred to cow rice tree because cows also eat the *Albizia julibrissin*.

The trunk of the tree is bent or lies a little sideways. The trees have a height of 3 to 5 meters, have large branches spread sparsely, and ridges in the small branches. There are two or three sprouts (hard scale pieces covering winter buds) of winter buds, but the sprouts are so small that they are hardly even visible. The leaves are alternate and two-pinnately compound leaves. Small leaves are bent like a sickle and are long ovals that are not the identical on the right and left sides, and the edges thereof are smooth. The small leaves have a length of approximately 6 to 15 mm and a width of approximately 2.5 to 4.0 mm, and have no fluffs on both sides thereof or have fluffs on the vein of the back surface.

The flowers are light pink and in bloom in June or July, and 15 to 20 flowers are each hung in the form of an umbrella at the end of small branches. The sepal and corolla are shallow and split into 5 pieces, and are greenish. There are around 25 stamens, which sprout longitudinally, and the upper part thereof is red. The flower looks crimson because of the color of the stamens. The fruit is ripe from the end of September to the beginning of October, is a flat pod, has a length of about 15 cm, and contains 5 or 6 seeds. A peculiar point is that in the case of shy plant or *mimosa*, leaves are attached to each other with the external stimulus, but in the case of the *Albizia julibrissin*, spread leaves face each other and fold when the sun goes down.

Licorice is a perennial herb belonging to the legume family, and is known as a medicinal plant often used as a herbal medicine in Asian countries. Glycyrrhizin is known as the main ingredient of licorice, and flavonid glycosides such as liquiritin and isoliquiritin, licoricidin which is an isoflavonoid, and the like have been reported. Licorice has been reported to have antioxidant, immune enhancing and antibacterial effects, and the like.

More preferably, the food composition of the present invention includes a composition for improving bone health, including the functional fermented material using oysters as a functional food composition, and may include 5 to 10 parts by weight of the *Albizia julibrissin* extract and 5 to 10 parts by weight of the licorice extract based on 100 parts by weight of the composition for improving bone health. Within the above ranges, off-taste and off-flavor such as seaweed odor slightly remaining may be removed. Further, a food composition with high preference may be provided due to the sweet taste of licorice. However, when the licorice extract is used in mixture with the *Albizia julibrissin* extract, the inherent sweet taste of licorice may be enhanced as compared to the case where only licorice is used.

According to the composition for improving bone health, including a functional fermented material using oysters according to the present invention, it is possible to provide a composition for improving bone health, containing large amounts of taurine and vitamins and containing natural gamma-aminobutyric acid (GABA) and seaweed oligosaccharides from seaweeds using oysters.

It is possible to provide a composition for improving bone health, including a functional fermented material using oysters which is excellent in effects of preventing and suppressing the occurrence of osteoporosis by suppressing the activity of osteoclasts and promoting the activity of osteoblasts to promote bone formation.

BRIEF DESCRIPTION OF THE DRAWINGS

FIGS. 3A, 3B and 3C are a set of results of effects of the composition for improving bone health according to an exemplary embodiment of the present invention on oxidative stress produced during the differentiation of osteoclasts.

DETAILED DESCRIPTION

Figure 1A:
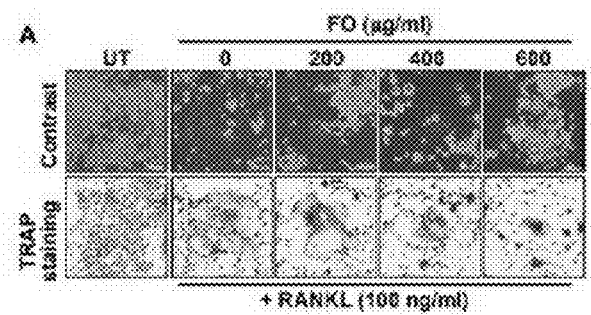
FIGS. 1A, 1B, 1C and 1D are a set of results of effects of the composition for improving bone health according to an exemplary embodiment of the present invention on the differentiation of osteoclasts.
Figure 1B:
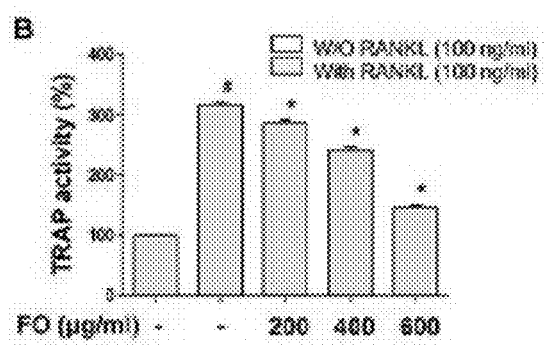
Figure 1C:
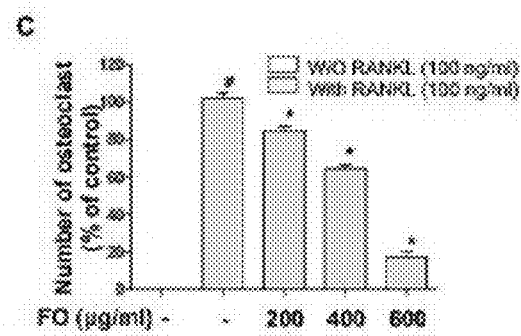
Figure 1D:
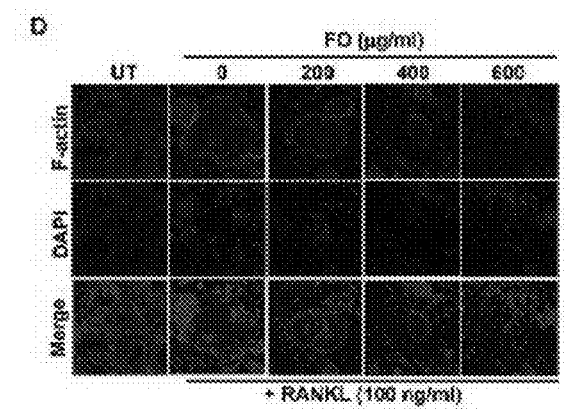

Hereinafter, the Examples of the present invention will be described in detail such that a person skilled in the art to which the present invention pertains can easily carry out the present invention. However, the present invention can be implemented in various different forms, and is not limited to the Examples described herein.

Preparation Example 1: Preparation of Composition for Improving Bone Health

1. Preparation of Composition (FO) for Improving Bone Health Using Raw Oysters and Algue Brune Impurities and salts were removed by washing and desalting raw oysters and algue brune. Thereafter, a mixed ground material of oysters and algue brune was prepared by drying and grinding raw oysters and algue brune.

After water was mixed with the mixed ground material of oysters and algue brune such that the content of the mixed ground material was 10 to 30% (v/v) based on the total weight, saprophytic bacteria were removed by sterilizing the mixture at 121° C. for 15 minutes. The mixture was cooled to 30 to 37° C. which is a temperature suitable for fermentation.

As a fermentation strain, *Lactobacillus brevis* BJ20 (Accession No.: KCTC 11377BP) and *Saccharomyces cerevisiae* MBP-27 were mixed and inoculated, and the inoculated mixture was fermented at a temperature of 30° C. to 37° C. In this case, a fermentation microbe was inoculated so as to have a content of 1 to 5% (v/v) based on the total weight, and the inoculated mixture was fermented for 2 to 7 days, such that the fermentation microbe was inoculated and the fermentation by the fermentation microbe sufficiently occurred. The logarithmically proliferated fermentation microbe during the fermentation period was killed by sterilizing a fermentation solution completely fermented at a high temperature of 121° C. under pressure for 15 to 20 minutes. Only a clear and clean fermentation solution was taken by finely filtering only water-soluble materials of 0.05 to 0.1 um from the sterilized fermentation solution. In order to prepare the finely filtered fermentation solution into a powder, the finely filtered fermentation solution was dried by a method such as spray drying or freeze drying, and then pulverized by grinding.

2. Preparation of Composition for Improving Bone Health Using Hydrolysate of Oysters and Algue Brune 2-1. Process of Preparing Hydrolysate of Oysters The oysters to be used were prepared by washing with water, desalting, and grinding so as to facilitate hydrolysis by enzymes. The pre-treated oysters and water were mixed at 1:1 and hydrolyzed by adding alcalase at 0.2% (v/v) thereto while stirring the mixture at 50 to 70° C. for 20 to 60 minutes. A residue of the hydrolyzed oysters was removed by a vibration sieve of 40 to 200 mesh and a hydrolysate of oysters was collected. Only water-soluble materials were finely filtered from the collected hydrolysate of oysters using an external circulation type vacuum separation membrane having a module with a pore size of 0.05 to 0.1 um.

2-2. Preparation of Composition for Improving Bone Health

Impurities and salts were removed by washing and desalting algue brune. Thereafter, a ground material of algue brune was prepared by drying and grinding algue brune, and was mixed with the hydrolysate of oysters in 2-1.

After water was mixed with the mixture of the hydrolysate of oysters and algue brune such that the content of the mixture was 10 to 30% (v/v) based on the total weight, saprophytic bacteria were removed by sterilizing the resulting mixture at 121° C. for 15 minutes. The mixture was cooled to 30 to 37° C. which is a temperature suitable for fermentation.

As a fermentation strain, *Lactobacillus brevis* BJ20 (Accession No.: KCTC 11377BP) and *Saccharomyces cerevisiae* MBP-27 were mixed and inoculated, and the inoculated mixture was fermented at a temperature of 30° C. to 37° C. In this case, a fermentation microbe was inoculated so as to have a content of 1 to 5% (v/v) based on the total weight, and the inoculated mixture was fermented for 2 to 7 days, such that the fermentation microbe was inoculated and the fermentation by the fermentation microbe sufficiently occurred. The logarithmically proliferated fermentation microbe during the fermentation period was killed by sterilizing a fermentation solution completely fermented at a high temperature of 121° C. under pressure for 15 to 20 minutes. Only a clear and clean fermentation solution was taken by finely filtering only water-soluble materials of 0.05 to 0.1 um from the sterilized fermentation solution. In order to prepare the finely filtered fermentation solution into a powder, the finely filtered fermentation solution was dried by a method such as spray drying or freeze drying, and then pulverized by grinding.

3. Preparation of Composition for Improving Bone Health Using Extracted Concentrate of Oysters and Algue Brune 3-1. Process of Preparing Extracted Concentrate of Oysters The oysters to be used were prepared by washing with water, desalting, and grinding so as to facilitate extraction. The pre-treated oysters were mixed with 10 to 20 times water and extracted while being stirred at 70 to 90° C. for 20 to 60 minutes. A residue of the extracted oysters was removed by a vibration sieve of 40 to 200 mesh and an extract of oysters was collected. Only water-soluble materials were finely filtered from the collected extract of oysters using an external circulation type vacuum separation membrane having a module with a pore size of 0.05 to 0.1 um. The finely filtered extract of oysters was concentrated such that the brix became 20 to 40% by reducing pressure at a temperature of 30 to 50° C.

3-2. Preparation of Composition for Improving Bone Health

Impurities and salts were removed by washing and desalting algue brune. Thereafter, a ground material of algue brune was prepared by drying and grinding algue brune, and was mixed with the concentrated extract of oysters in 3-1.

After water was mixed with the mixture of the hydrolysate of oysters and algue brune such that the content of the mixture was 10 to 30% (v/v) based on the total weight, saprophytic bacteria were removed by sterilizing the resulting mixture at 121° C. for 15 minutes. The mixture was cooled to 30 to 37° C. which is a temperature suitable for fermentation.

As a fermentation strain, *Lactobacillus brevis* BJ20 (Accession No.: KCTC 11377BP) and *Saccharomyces cerevisiae* MBP-27 were mixed and inoculated, and the inoculated mixture was fermented at a temperature of 30° C. to 37° C. In this case, a fermentation microbe was inoculated so as to have a content of 1 to 5% (v/v) based on the total weight, and the inoculated mixture was fermented for 2 to 7 days, such that the fermentation microbe was inoculated and the fermentation by the fermentation microbe sufficiently occurred. The logarithmically proliferated fermentation microbe during the fermentation period was killed by sterilizing a fermentation solution completely fermented at a high temperature of 121° C. under pressure for 15 to 20 minutes. Only a clear and clean fermentation solution was taken by finely filtering only water-soluble materials of 0.05 to 0.1 um from the sterilized fermentation solution. In order to prepare the finely filtered fermentation solution into a powder, the finely filtered fermentation solution was dried by a method such as spray drying or freeze drying, and then pulverized by grinding.

Experimental Example 1: Suppression of Activity of Osteoclasts

1. Culture and Differentiation of Osteoclasts

RAW 264.7 cells, which is a murine macrophage cell line used in the present study, were cultured in a $CO_2$ incubator (37° C., 5% $CO_2$) using Dulbecco's modified Eagle's media (DMEM; Gibco BRL, Gaithersburg, Md., USA) including 10% fetal bovine serum (FBS) and 1% penicillin-streptomycin for cell culture.

By using RAW 264.7 as an osteoclast progenitor cell, a culture solution in which RANKL as a differentiation factor at 100 ng/mL and the composition for improving bone health (hereinafter, referred to as FO) using raw oysters and algue brune were mixed so as to have a concentration of 0, 200, 400, and 600 μg/mL was aliquoted into the α-MEM media supplemented with 10% FBS, and RAW 264.7 was cultured for 5 days while exchanging the media every two days.

2. Measurement of Production of Osteoclasts

After RAW 264.7 cells were stabilized in DMEM for 24 hours, RAW 264.7 cells were aliquoted by adding RANKL (100 ng/mL) and FO at each concentration of 0, 200, 400, and 600 μg/mL to the α-MEM. On day 5, TRAP positive cells were acknowledged as osteoclasts by staining with a TRAP solution. The number of cells containing three or more nuclei among the stained osteoclasts was used in the statistics.

3. Measurement of Actin Ring Formation

After RAW 264.7 cells were differentiated into osteoclasts by treatment with RANKL (100 ng/mL), the osteoclasts were treated with FO at each concentration of 0, 200, 400, and 600 μg/mL while being cultured in α-MEM, matured osteoclasts were stained with Alexa Fluor 488-conjugated phalloidin, and then stained with DAPI for 30 minutes. Actin ring and DAPI staining was observed by a fluorescence microscope.

4. Western Blot Analysis

In order to observe the signal transduction process by RANKL, RAW 264.7 cells were lysed with a lysis buffer (50 mM tris-Cl, 150 mM NaCl, 5 mM EDTA, 1% Triton X-100, 1 mM sodium fluoride, 1 mM sodium vanadate, 1% deoxycholate, and protease inhibitors). A supernatant was obtained by centrifuging (14,000 rpm, 30 min) the entire lysate. After the supernatant was weighed, the supernatant was separated by SDS-PAGE and transferred to a PVDF membrane, and then allowed to react using a specific antibody, and the expression level of proteins was confirmed using an image analyzer.

5. Measurement of Production of ROS in Cells

After RAW 264.7 cells were aliquoted at $5 \times 10^4$ cells/well into 6-well plates and stabilized for 24 hours, RAW 264.7 cells were induced into differentiation by RANKL (100 ng/mL), treated with FO at each concentration, cultured for 5 days, and then stained at 37° C. for 30 minutes by treatment with 10 μM DCF-DA, and then measured using flow cytometry.

6. Effects of FO on the Differentiation of Osteoclasts Induced by RANKL (FIG. 1)

RAW 264.7 cells were treated with RANKL to induce differentiation into osteoclasts, and the effects of FO on the differentiation and production of osteoclasts were measured by treatment with FO at various concentrations (0, 200, 400, and 600 μg/ml). As a result of observing TRAP staining of osteoclasts by a microscope, it could be confirmed that as the concentration of FO was increased, the size of TRAP positive cells was decreased (A). And, as a result of measuring the number of TRAP positive cells, it was observed that the number of TRAP positive cells was suppressed in a concentration-dependent manner in the same manner as described above (B, C). Since the actin of osteoclasts is organized as one big ring in order to divide a general extracellular space while osteoclasts perform bone formation during the bone resorption process and are attached to bones, the formation of the actin ring is an important mark for the ability of osteoclasts to resorb bones. As a result of observing the formation of the acting ring by treating differentiated osteoclasts with FO at each concentration, it was confirmed that the formation of the actin ring was suppressed in a concentration-dependent manner (D).

Figure 2A:
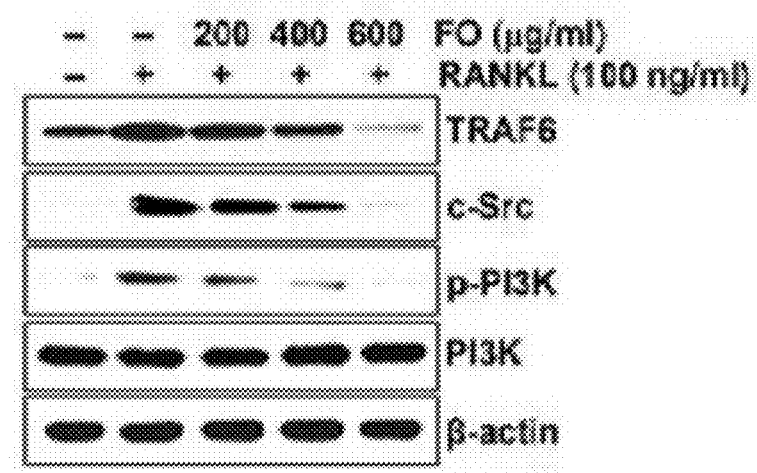
FIGS. 2A, 2B and 2C are a set of results of effects of the composition for improving bone health according to an exemplary embodiment of the present invention on the expression of proteins associated with the differentiation of osteoclasts.
Figure 2B:
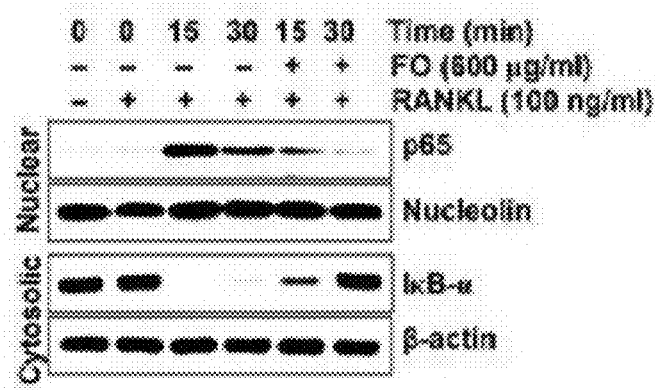
Figure 2C:
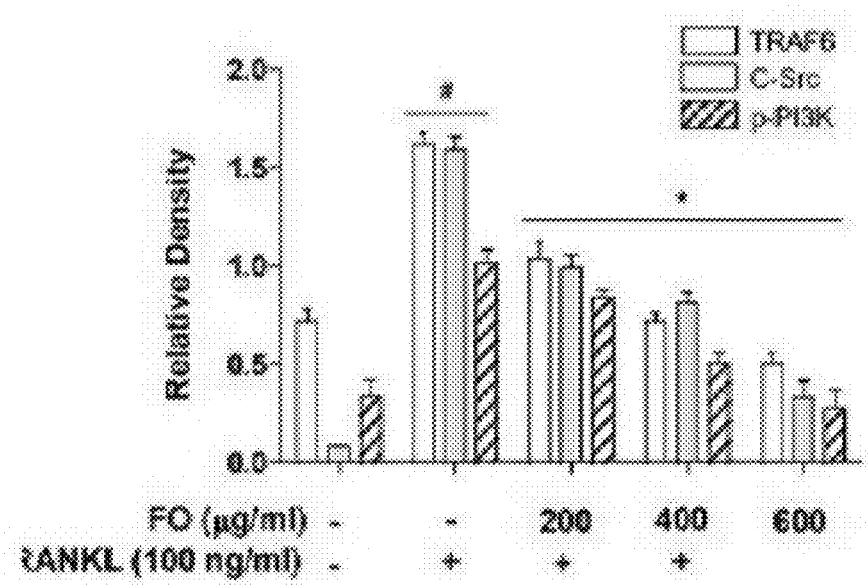

7. Effects of FO on Expression of Proteins Associated with Differentiation of Osteoclasts (FIG. 2)

After the formation of osteoclasts was induced using RANKL (100 ng/mL) in RAW 264.7 cells, the expressions of proteins associated with differentiation by FO were compared. It could be seen that the expression of TRAF6 and c-Src which are important signal transduction factors for the signal transduction system by RANKL was decreased in a FO concentration-dependent manner, and the phosphorylation of PI3K was also regulated. And, it was confirmed that during the differentiation of osteoclasts, RANKL increased the expression of IκB-α and promoted the nuclear translocation of p65, whereas the expression was suppressed in the FO treatment group. It can be seen that FO suppresses the NF-kB pathway which is a transcription factor essential for the osteoclast differentiation process.

8. Effects of FO on Oxidative Stress Produced During the Differentiation of Osteoclasts (FIG. 3)

It is known that oxidative stress in cells occurs during the differentiation of osteoclasts induced by RANKL. Therefore, the effects of FO on the production of ROS induced by RANKL was confirmed through DCF-DA staining. ROS increased in the osteoclasts treated with RANKL was remarkably decreased in the FO treatment group. It was confirmed using a microscope that this phenomenon was also similarly observed even in NAC which is an antioxidant.

Figure 4A:
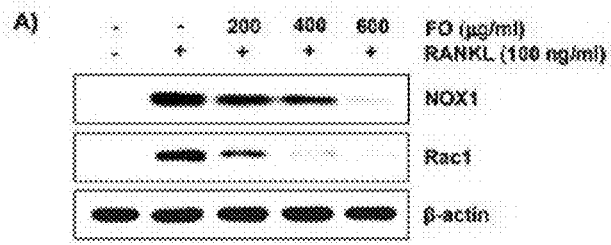
FIGS. 4A, 4B and 4C are a set of results of the change in expression of osteoclast-associated proteins by suppressing the production of ROS by the composition for improving bone health according to an exemplary embodiment of the present invention.
Figure 4B:
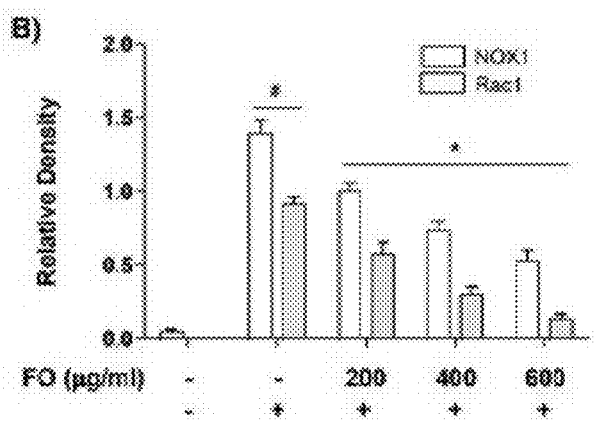
Figure 4C:
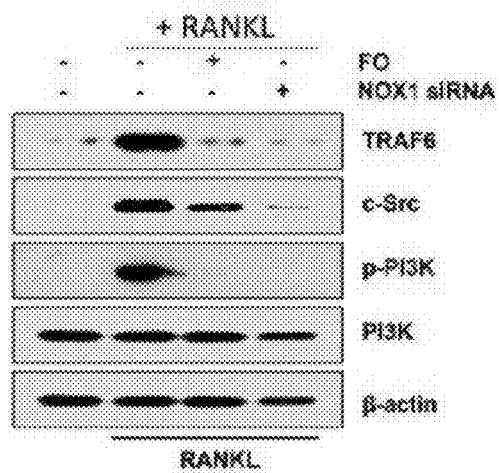

9. Change in Expression of Osteoclast-Associated Proteins by Suppressing Production of ROS by FO (FIG. 4)

The NADPH oxidase is one of the main factors of ROS, and among the NOXs constituent members, the expression of NOX1 involved in the production of osteoclasts and a regulatory protein Rac1 was decreased in a FO concentration-dependent manner. In order to confirm the role of NOX1 in effects of FO on the differentiation of osteoclasts, the expression of proteins associated with the differentiation of osteoclasts was analyzed by silencing NOX1. As a result, it was confirmed that TRAF6, c-Src, and p-PI3K signals induced by RANKL were decreased in the FO treatment group, and considerably suppressed in the NOX1 si RNA and FO groups. Therefore, FO may suppress the osteoclast differentiation signal transduction mechanism by inhibiting the NOX1-dependent production of ROS induced by RANKL.

Experimental Example 2: Induction of Activation of Osteoblasts

1. Culture and Distribution of Osteoblasts

MC3T3-E1 cells used in the present experiment are mouse calvaria-derived osteoblasts and were purchase from the American Type Culture Collection Manassas (ATCC, VA, USA), and the α-minimum essential medium (α-MEM) medium, fetal bovine serum (FBS), penicillin-streptomycin, and the like required for the culture of cells were purchased from GIBCO (Invitrogen, Carlsbad, Calif., USA). The MC3T3-E1 cells were cultured in a $CO_2$ incubator at 37° C. using the α-MEM medium supplemented with 10% FBS and 1% antibiotic (penicillin-streptomycin). The media were exchanged for the first time after two days, and then exchanged every four days. When the primary culture cells reached a density of 70 to 80% after 2 to 3 days of culture, the primary culture cells were sub-cultured using a 0.025% trypsin solution.

2. MTT Assay

The proliferation degree of osteoblasts was measured by MTT assay, which obtains the survival rate of living cells. After 100 μl of MC3T3-E1 cells were each aliquoted at a concentration of $1 \times 10^4$ cells/well into 96 well plates, and then cultured in a $CO_2$ incubator at 37° C. for 24 hours, the medium was removed, and a new culture solution prepared by distributing FO at various conditions (0, 50, 100, and 200 μg/ml) was aliquoted into a medium which was not supplemented with FBS. After 48 hours of culture, the medium was removed, an MTT reagent (10 μl/well) at a concentration of 0.05 mg/ml was aliquoted, and then after the cells were further cultured for 4 hours, the culture solution was removed and the precipitate was dissolved in dimethyl sulfoxide (DMSO) to measure the absorbance at 570 nm using a microplate reader (Bio-rad, Benchmark, Hercules, Calif., USA). A control was cultured by putting a medium which was not supplemented with a sample, and the survival rate of cells was calculated based on the absorbance of the control.

3. Measurement of Activity of Alkaline Phosphatase of Osteoblasts

MC3T3-E1 cells were inoculated at $1 \times 10^4$ cells per well into 96-well culture plates and cultured for 24 hours, and cultured for 48 hours by exchanging the medium with a medium containing FO at various concentrations (0, 50, 100, and 200 μg/ml). The culture solution was removed, and the cells were lysed with 1% Triton X-100 and sonicated. After 50 μl/well of a buffer solution containing 0.4 mM tris-HCl, 2 mM $MgCl_2$, and 4 mM p-nitrophenol phosphate (PNPP) was added thereto, the cells were allowed to react for 30 minutes, the reaction was terminated by adding 150 μl of 1 N NaOH thereto, and then the absorbance of decomposed p-nitrophenol (PNP) was measured at 405 nm using a microplate reader (Bio-rad, Benchmark, Hercules, Calif., USA). The amount of protein was measured using a bovine serum albumin protein assay reagent, and the enzyme activity was expressed as a percentage relative to the control.

4. Measurement of Promotion of Bone Formation in Zebrafish Model

In order to confirm an effect of FO in vivo on the promotion of bone formation, the zebrafish fed with FO at various concentrations (0, 50, and 100 μg/ml) for 35 days were exposed to calcein and stained.

Specifically, the zebrafish fed with FO at various concentrations (0, 50, and 100 μg/ml) and the zebrafish fed with no FO were exposed to calcein and stained, when the zebrafish were appropriately stained, the solution was discarded, and the zebrafish were washed with PBS, and then dried. Subsequently, images were obtained using a Nikon Eclipse Ti microscope, and the effect of FO in vivo on the promotion of bone formation was evaluated by measuring the staining intensity among the images.

Figure 5:
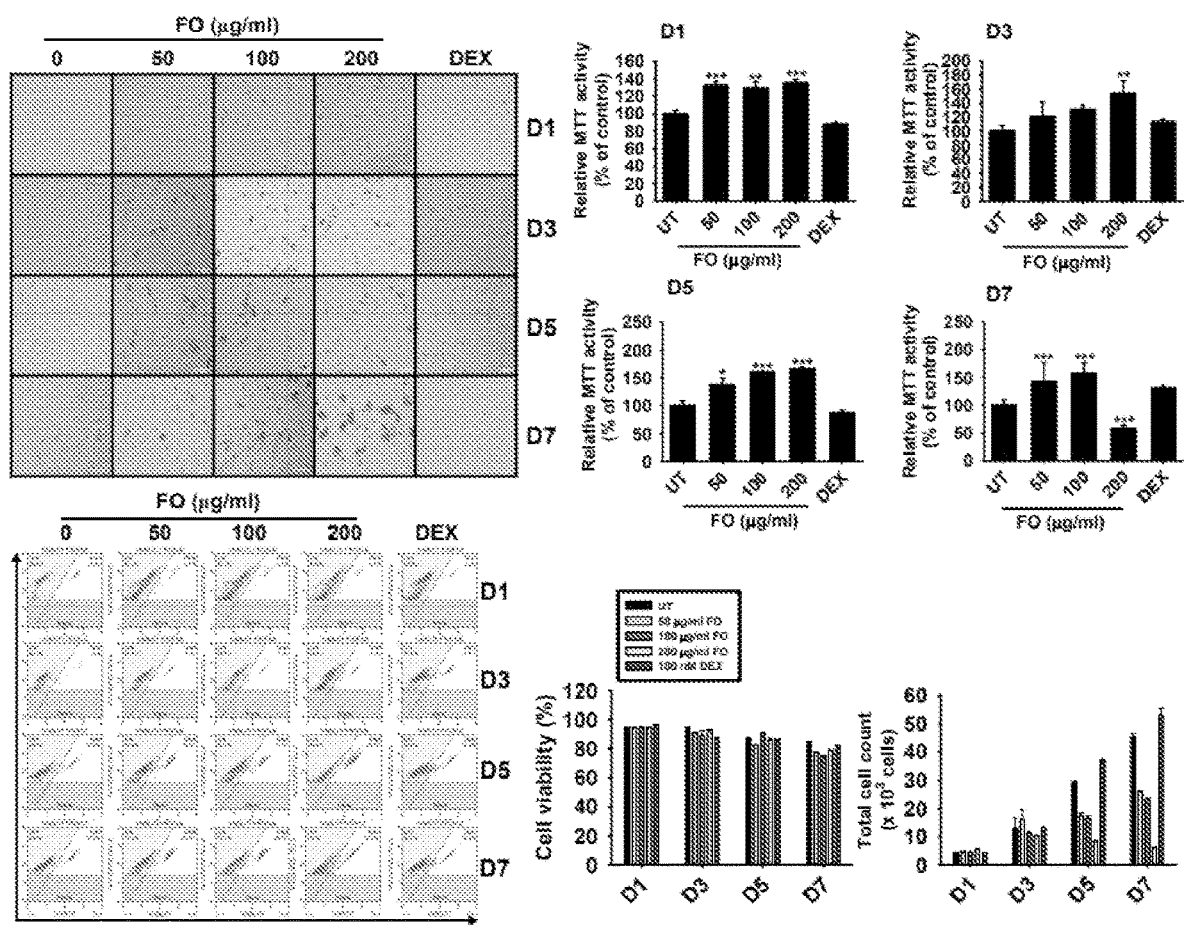
FIG. 5 is a set of results of effects of the composition for improving bone health according to an exemplary embodiment of the present invention on osteoblasts (MTT assay).

5. Effects of FO on Osteoblasts (FIG. 5)

In the FO treatment group, it could be confirmed that a clump was formed between cells from day 3, and MTT activation was rapidly increased from day 3. As a result of confirming the effects on the change in the actual number of total cells and the survival of cells, the survival rate of total cells was shown to be the same as that of the group which was not treated with the drug during the experimental time, but the number of total cells was noticeably reduced from day 5 (the number of total cells was reduced due to the differentiation into osteoblasts).

Figure 6:
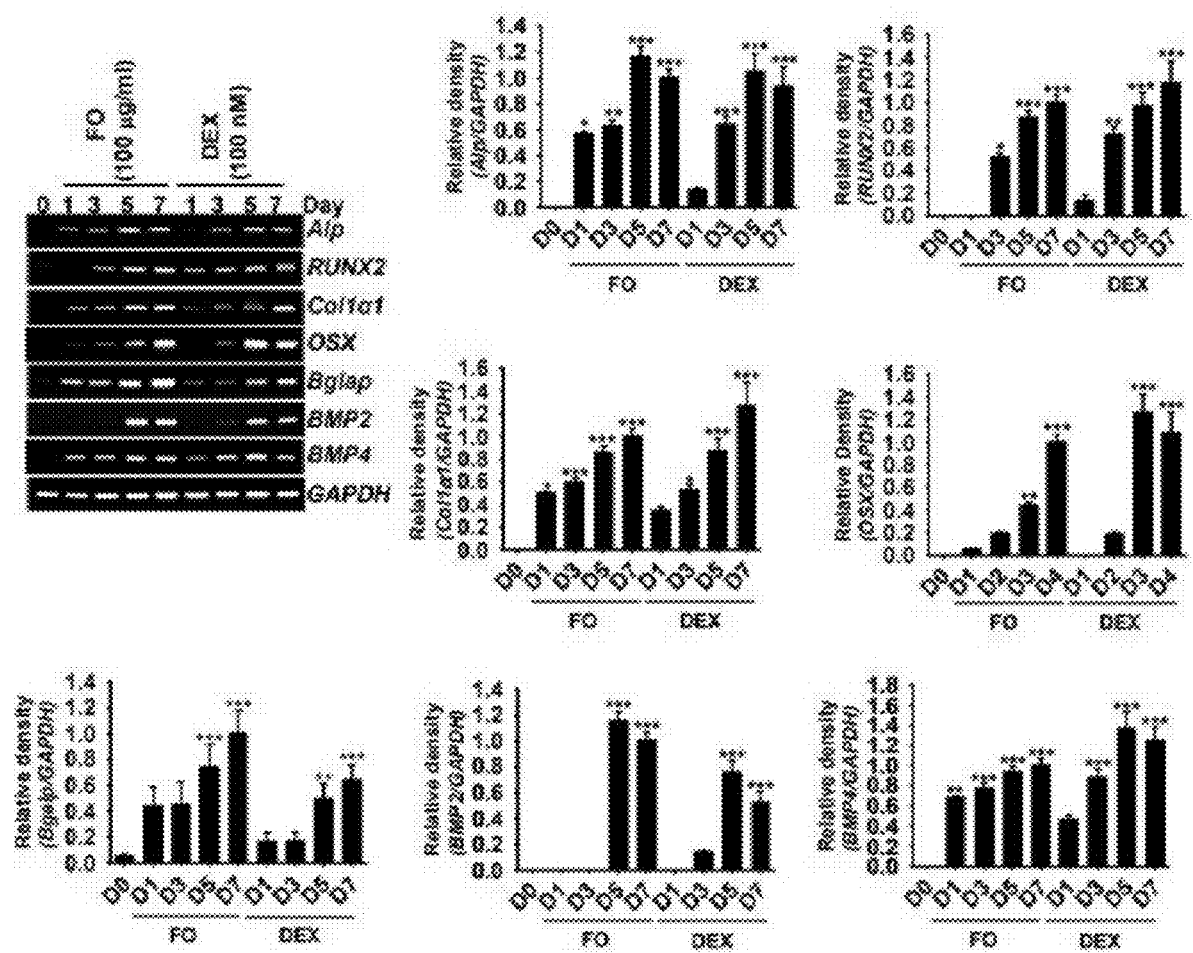
FIG. 6 is a set of results of effects of the composition for improving bone health according to an exemplary embodiment of the present invention on the differentiation of essential genes required for the formation of osteoblasts.
Figure 7:
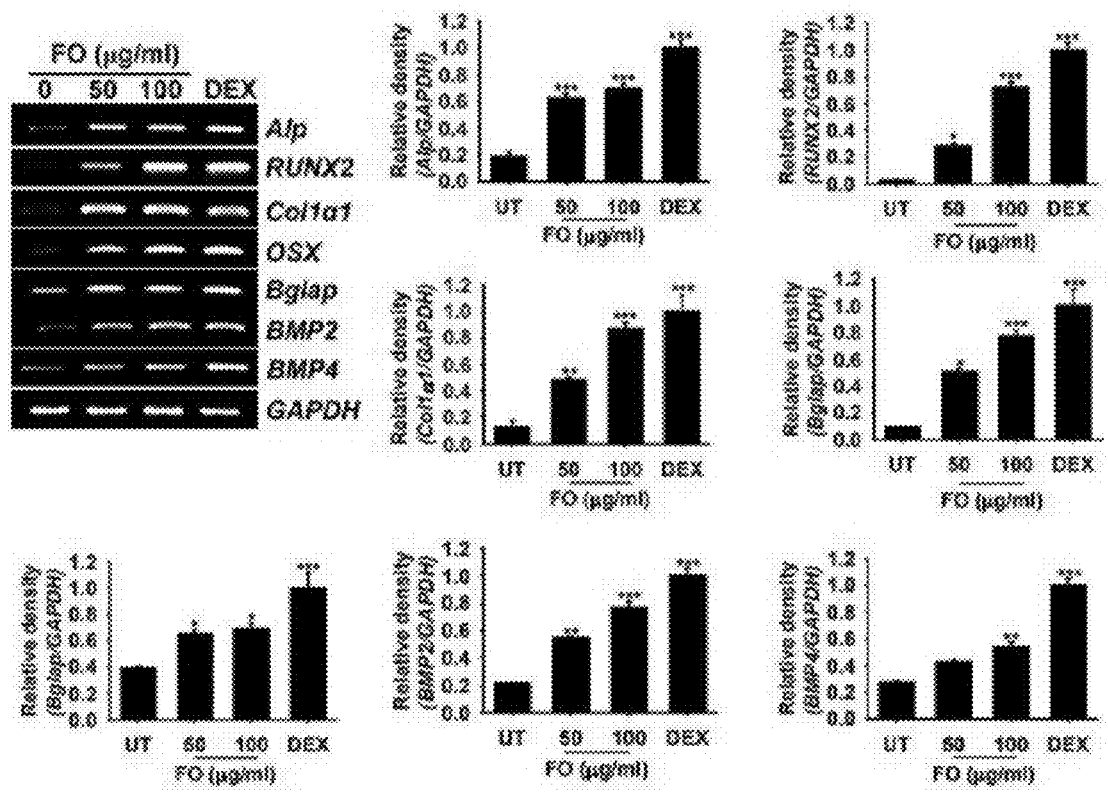
FIG. 7 is a set of results of effects of the composition for improving bone health according to an exemplary embodiment of the present invention on the differentiation of essential genes required for the formation of osteoblasts.

6. Effects of FO on Expression of Genes Essential for Formation of Osteoblasts (FIGS. 6 and 7)

After a treatment in order to understand the effect of FO (100 ug/ml) on the expression of genes essential for the formation of osteoblasts, as a result of confirming the expression of genes on days 1, 3, 5, and 7 after treatment for 7 days, the expression of Alp, RUNX2, Col1a1, OSX, Bglap, $BMP_2$, and BMP was strongly increased.

Figure 8:
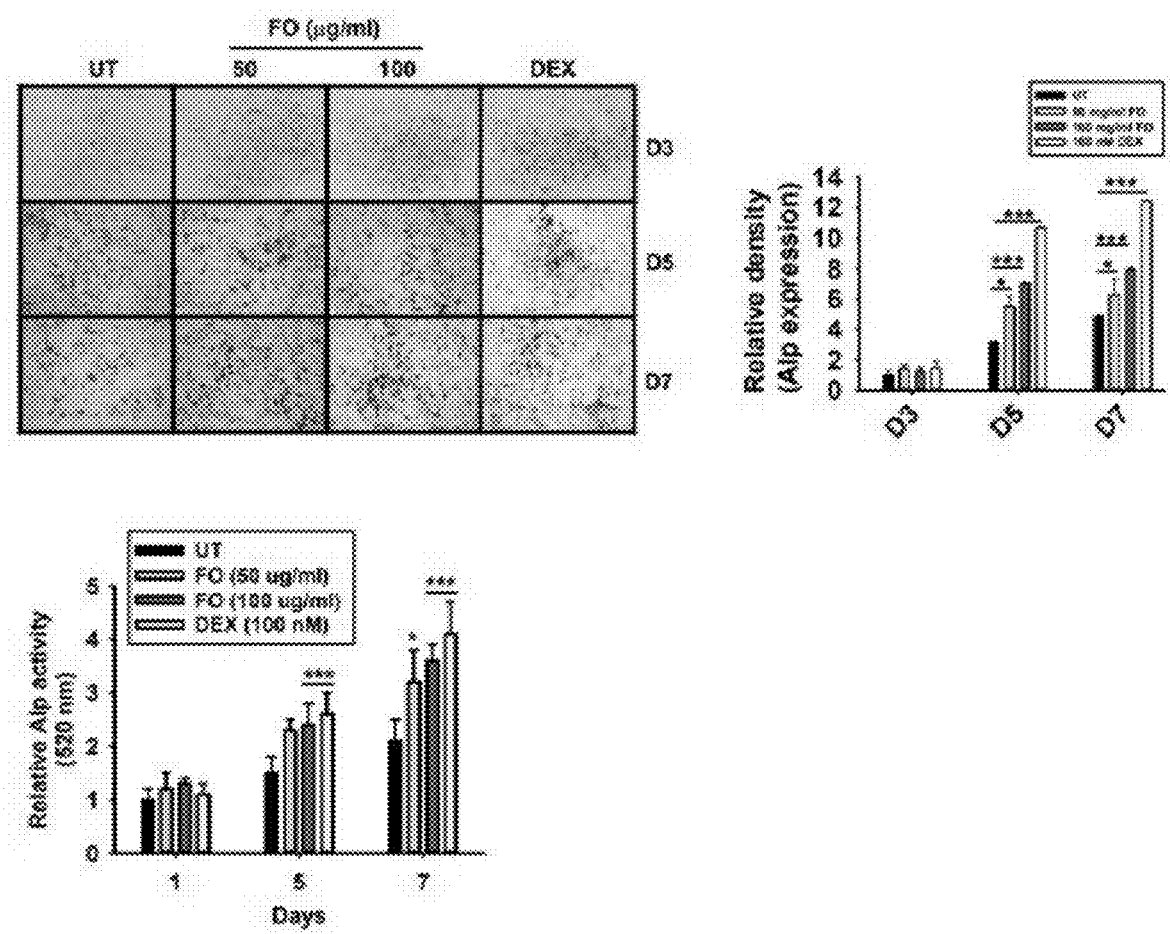
FIG. 8 is a set of results of the Alp activation of the composition for improving bone health according to an exemplary embodiment of the present invention.

7. Alp Activation which is Core Factor for Bone Formation (FIG. 8)

The synthesis of ALP, which increases the concentration of local phosphoric acid ions, was measured at a site where bone reformation and regeneration occurred by administering FO at 50 μg/ml and 100 μg/ml to MC3T3-E1 cells. On day 3, there was no significant difference between the experimental group and the control, but the ALP activity was significantly increased in the two FO treatment group from day 5. Dex was used as a positive control.

Figure 9:
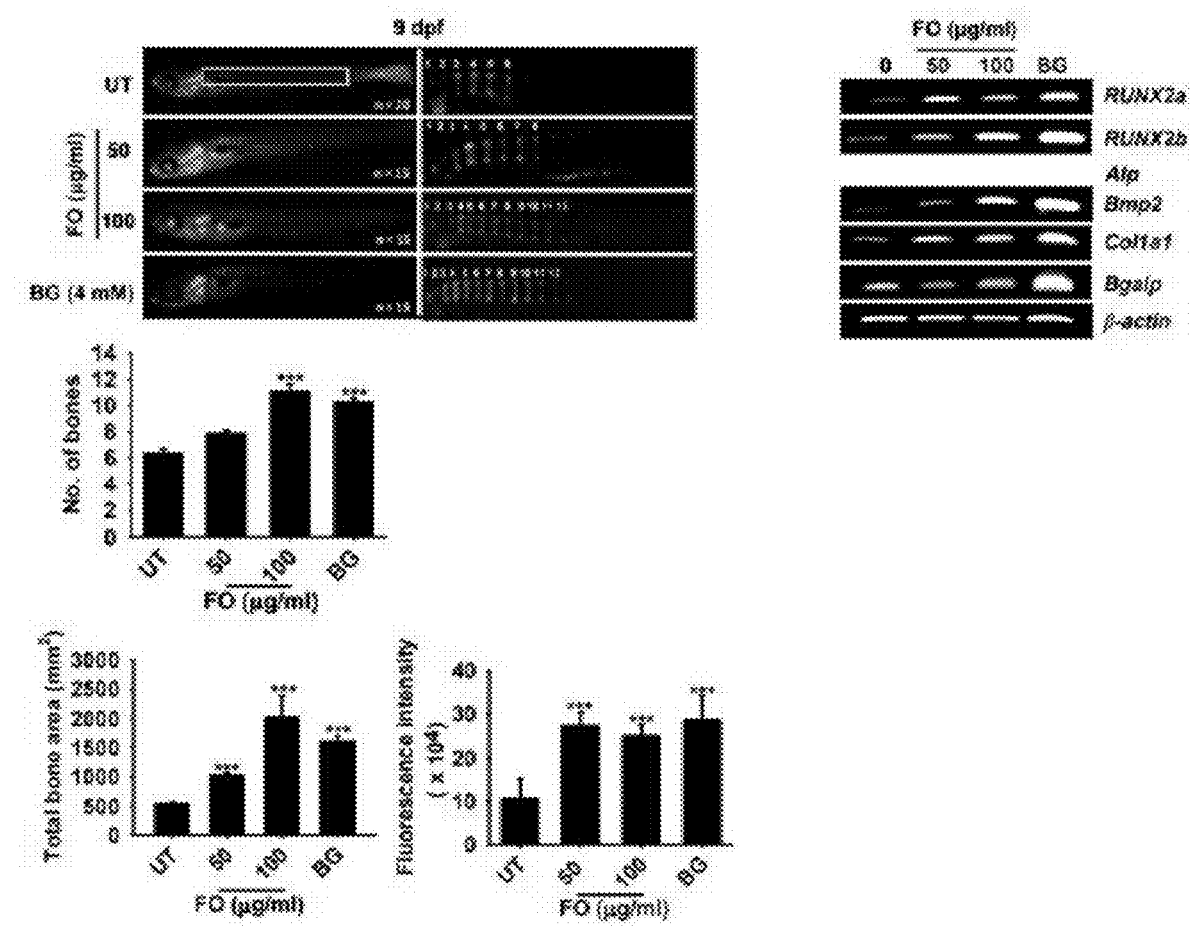
FIG. 9 is a set of results of the composition for improving bone health according to an exemplary embodiment of the present invention on the promotion of bone formation in the generation step of zebrafish.
Figure 10:
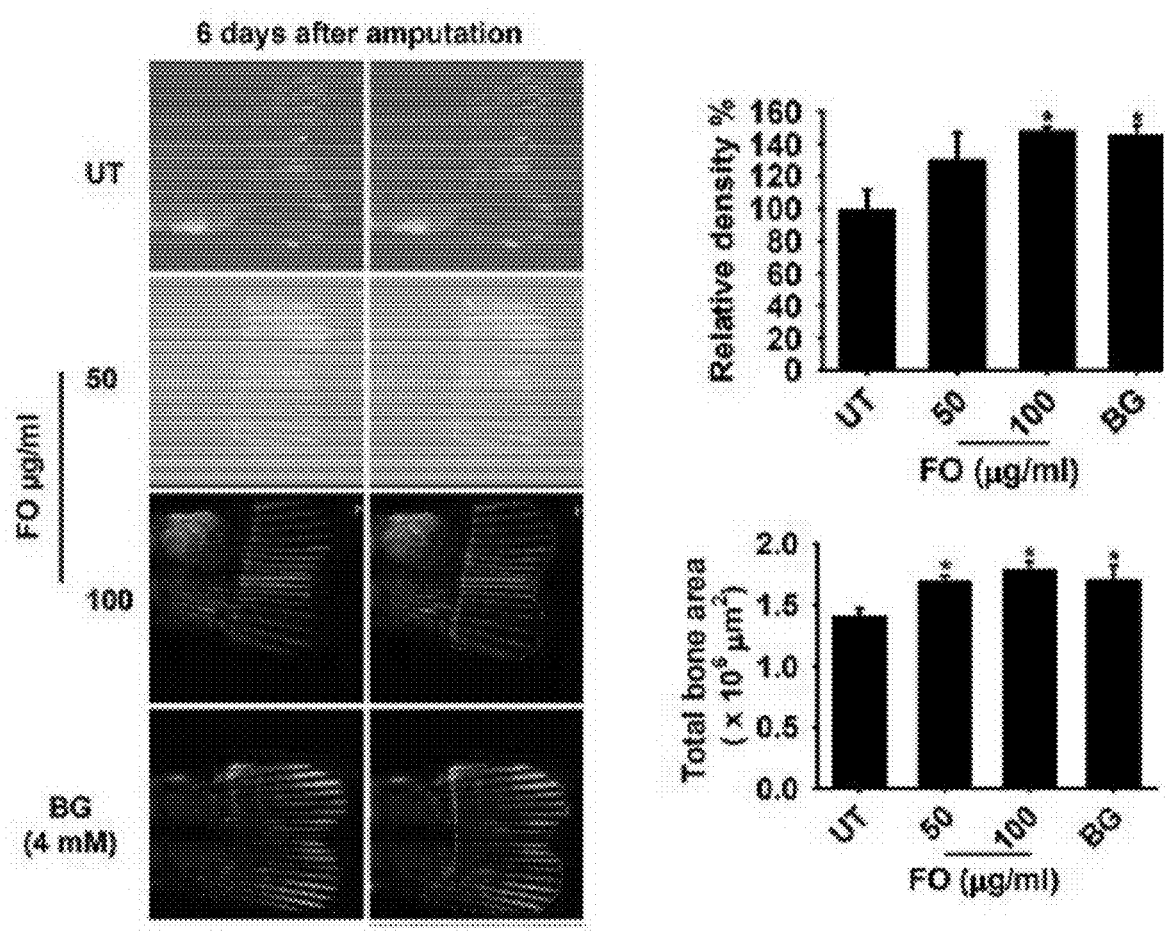
FIG. 10 is a set of results of the composition for improving bone health according to an exemplary embodiment of the present invention on the promotion of bone formation in the generation step of zebrafish.

8. Promotion of Bone Formation in Generation Step of Zebrafish (FIGS. 9 and 10)

After treatment with FO (50 ug/ml and 100 ug/ml) from day 3 to day 9, bone formation was confirmed in the zebrafish. About 9 days later, it was confirmed that the formation of the vertebrae was promoted by treatment with FO. It was confirmed that the area and fluorescence intensity of the vertebrae entirely produced were also increased.

Experimental Example 3: Therapeutic Effect of Osteoporosis in Ovariectomy Model

1. Manufacture of Osteoporosis Animal Model

After 8-week-old female ICR mice were purchased and acclimatized for one week, the mice were divided into 5 groups of 8 animals each for experiments.

The respective groups were classified into 1) a non-ovariectomy normal control (Sham) in which the skin and the muscle layer were sutured without taking out the ovaries, 2) a control (OVX) in which osteoporosis was caused by excising the ovaries, 3) an experimental group (OVX+FO 100 mg/kg) in which FO was orally administered at 100 mg/kg each daily after the excision of the ovaries, 4) an experimental group (OVX+FO 200 mg/kg) in which FO was orally administered at 200 mg/kg each daily after the excision of the ovaries, and 5) a positive control (OVX+E2) in which 17-beta-estradial (E2) was intraperitoneally administered daily after the excision of the ovaries.

After the ICR mice were anaesthetized with Avertin, the hairs on the backs of the mice were removed, the skin and the muscle layer were excised with a pair of fine scissors, and then the ovaries on both sides were completely excised and sutured with sutures.

2. Micro-CT Analysis

After the experimental animals were sacrificed and the tibias were taken out and fixed 4 weeks after the ovariectomy, 3-D video images were reconstructed using micro-CT (Skyscan 1272, Bruker, Kontich, Belgium), and various bone indices (BMD, BV/TV, Tb.N, Tb.Th, and Tb.Sp) were analyzed.

Figure 11:
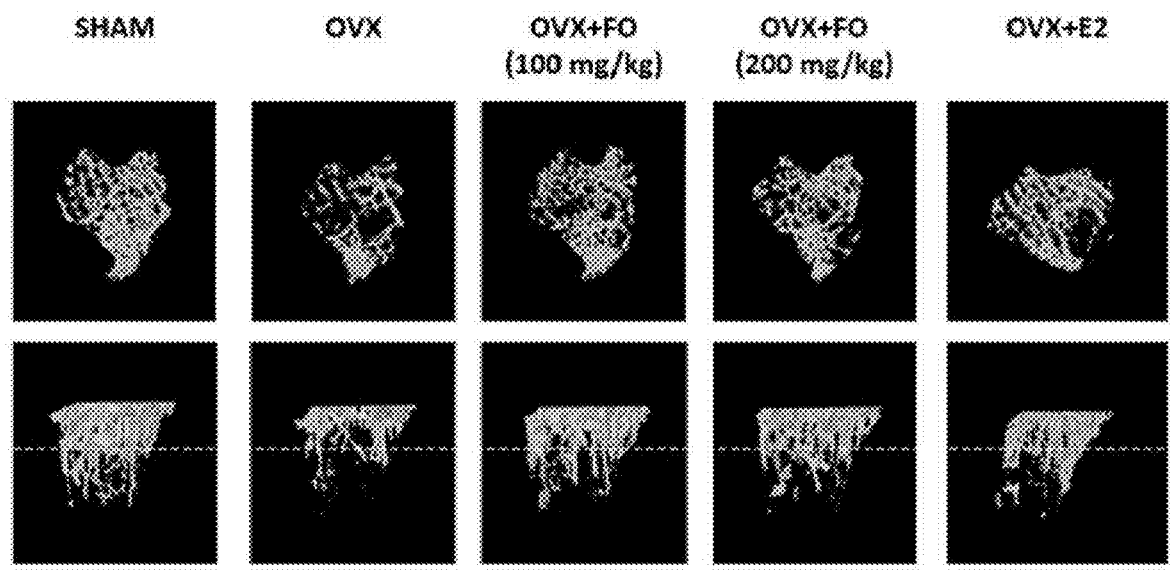
FIG. 11 is a set of results of 3D video images of the composition for improving bone health according to an exemplary embodiment of the present invention obtained by using micro-CT.
Figure 12:
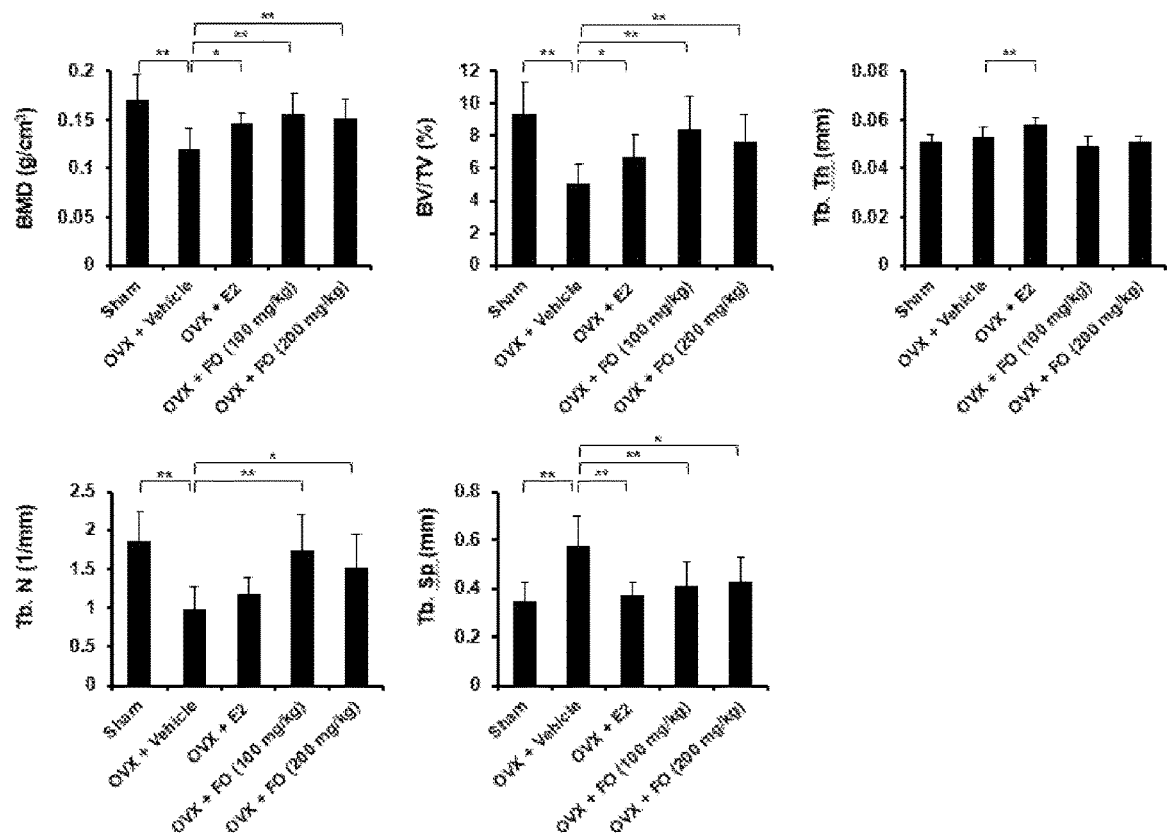
FIG. 12 is a set of results of effects of the composition for improving bone health according to an exemplary embodiment of the present invention on bone trait variables of the tibia.

3. Therapeutic Effect of Osteoporosis (FIGS. 11 and 12)

Through the 3-D video images obtained by Micro-CT, the bone loss was more severe in the control in which osteoporosis was caused than in the non-ovariectomy normal control, and the bone loss was suppressed in all the groups to which FO was orally administered at 100 mg/kg and 200 mg/kg.

It was shown that the administration of FO had a significant improvement effect in bone density (BMD) and bone volume (BV/TV (%)). Further, it was confirmed that the trabecular number, trabecular separation, and trabecular thickness were also significantly recovered.

Therefore, it is determined that FO exhibits effective effects on the improvement of osteoporosis.

Experimental Example 4: Comparison of Effects of Composition for Improving Bone Health on Improvement of Bone Health 1. Preparation of Composition (FO') for Improving Bone Health Using Raw Oysters and Algue Brune Impurities and salts were removed by washing and desalting raw oysters and algue brune. Thereafter, a mixed ground material of oysters and algue brune was prepared by drying and grinding raw oysters and algue brune. Thereafter, a composition for improving bone health was prepared in the same manner as in Preparation Example 1, except that as fermentation strains, *Lactobacillus fermentum* JS and *Aspergillus* Usamii were used.

2. Preparation of Composition (FM1) for Improving Bone Health

A composition (FM1) for improving bone health was prepared by mixing FO and FO' at a weight ratio of 1:0.5.

3. Preparation of Composition (FM2) for Improving Bone Health

A composition (FM2) for improving bone health was prepared by mixing FO and FO' at a weight ratio of 1:1.

4. Preparation of Composition (FM3) for Improving Bone Health

A composition (FM3) for improving bone health was prepared by mixing FO and FO' at a weight ratio of 1:2.

2. Comparison of Effects of Suppressing Formation of Osteoclasts

The effects of FO, FO', FM1, FM2, and FM3 on the suppression of formation of osteoclasts were compared and evaluated. The effect of FO on the suppression of formation of osteoclasts was set to an index of 5, and degrees to which FO', FM1, FM2, and FM3 suppressed the formation of osteoclasts were evaluated and expressed as indices.

A higher index means that the effect is excellent.

TABLE 1

| | Suppression of osteoclast differentiation | Expression of proteins associated with differentiation of osteoclasts | Oxidative stress | Change in expression of proteins associated with osteoclasts by suppression of ROS production |
|---|---|---|---|---|
| FO | 5 | 5 | 5 | 5 |
| FO' | 6 | 7 | 7 | 7 |
| FM1 | 3 | 4 | 3 | 3 |
| FM2 | 8 | 8 | 8 | 7 |
| FM3 | 5 | 5 | 4 | 5 |

(Unit index) According to Table 1, it was confirmed that according to the difference in fermentation strains, the effect of FO' on the suppression of the formation of osteoclasts was better than that of FO on the suppression of the formation of osteoclasts.

More specifically, after the treatment with FO and FO' in the same concentration range, the formation of an actin ring was observed, but it was confirmed that the formation of the actin ring was suppressed in FO' as compared to in FO, so that it was confirmed based on the result that the differentiation of osteoclasts was suppressed.

The expression of TRAF6 and c-Src as signal transduction factors was decreased in FO' as compared to in FO, and the phosphorylation of PI3K was regulated. Further, it was confirmed that the effect of FO' on the suppression of the NF-kB pathway was better than that of FO on the suppression of the NF-kB pathway.

It was confirmed that ROS increased in the RANKL-treated osteoclasts was remarkably decreased in FO' as compared to in FO and the TRAF6, c-Src, and p-PI3K signals induced by RANKL were further decreased in the FO' treatment group, so that in summary, the effect of FO' on the suppression of formation of osteoclasts is better than that of FO.

It was confirmed that FM 1 to FM 3 in which FO and FO' were mixed exhibited the difference in effect of suppressing the formation of osteoclasts according to the mixing ratio of FO and FO', and among them, FM2 exhibited the best effect.

3. Comparison of Effects of Inducing Activation of Osteoblasts

Effects of FO and FO' on the induction of activation of osteoblasts were compared and evaluated. The effect of FO on the induction of activation of osteoblasts was set to an index of 5, and degrees to which FO', FM1, FM2, and FM3 induced the activation of osteoblasts were evaluated and expressed as indices.

A higher index means that the effect is excellent.

TABLE 2

| | Number of total cells | Expression of essential genes (expression of Alp, RUNX2, Col1a1, OSX, Bglap, BMP2, and BMP) | Alp activation | Promotion of bone formation (generation step of zebrafish) |
|---|---|---|---|---|
| FO | 5 | 5 | 5 | 5 |
| FO' | 7 | 7 | 7 | 7 |
| FM1 | 4 | 4 | 4 | 3 |
| FM2 | 8 | 8 | 8 | 7 |
| FM3 | 5 | 5 | 5 | 5 |

(Unit index) According to Table 2, it was confirmed that according to the difference in fermentation strains, the effect of FO' on the induction of the activation of osteoblasts was better than that of FO on the induction of the activation of osteoblasts.

More specifically, it was confirmed through experiments that due to the differentiation of osteoblasts, a decrease in number of total cells was marked in FO' as compared to in FO, and the expression of essential genes was also increased in FO' as compared to in FO.

It was confirmed that the Alp activity, which is a core factor for bone formation, was also increased in FO' as compared to in FO, and the area and fluorescence intensity of the vertebrae in the generation step of zebrafish were also increased considerably.

It was confirmed that FM 1 to FM 3 in which FO and FO' were mixed exhibited the difference in effect of inducing the activation of osteoblasts according to the mixing ratio of FO and FO', and among them, FM2 exhibited the best effect.

Although preferred Examples of the present invention have been described in detail hereinabove, the right scope of the present invention is not limited thereto, and it should be understood that many variations and modifications of those skilled in the art using the basic concept of the present invention, which is defined in the following claims, will also fall within the right scope of the present invention.

What is claimed is:

1. A composition for promoting bone formation, the composition comprising a fermented extract extracted from a fermented material,
    wherein
    the fermented material is obtained by fermenting oysters and a seaweed,
    the fermented material is fermented using a fermentation microbe, and the fermentation microbe is a mixture of *Lactobacillus brevis* BJ20 (Accession No.: KCTC 11377BP) and *Saccharomyces cerevisiae* MBP-27,
    the fermented extract promotes bone formation by suppressing the activity of osteoclasts and promoting the activity of osteoblasts, and
    the seaweed is algue brune.

2. The composition of claim 1, wherein the fermented extract further comprises taurine and gamma-aminobutyric acid (GABA).

3. The composition of claim 1, wherein the oysters are selected from the group consisting of raw oysters, a hydrolysate of oysters, an extracted concentrate of oysters, and a mixture thereof.

4. A pharmaceutical composition comprising a functional fermented material, comprising the composition for improving bone health according to claim 1.

5. A food composition comprising a functional fermented material, comprising the composition for improving bone health according to claim 1.

* * * * *